United States Patent [19]

Krüger et al.

[11] Patent Number: 4,548,931

[45] Date of Patent: Oct. 22, 1985

[54] THIOPHOSPHONIC ACID ESTER PESTICIDES

[75] Inventors: Bernd-Wieland Krüger, Wuppertal; Bernhard Homeyer, Leverkusen; Ingeborg Hammann, Muelheim; Wilhelm Stendel, Wuppertal, all of Fed. Rep. of Germany

[73] Assignee: Bayer Aktiengesellschaft, Leverkusen, Fed. Rep. of Germany

[21] Appl. No.: 538,856

[22] Filed: Oct. 4, 1983

[30] Foreign Application Priority Data

Oct. 16, 1982 [DE] Fed. Rep. of Germany ....... 3238363

[51] Int. Cl.$^4$ .......................... A01N 57/04; C07F 9/40
[52] U.S. Cl. .................................. 514/141; 260/955; 260/961; 260/940; 260/960
[58] Field of Search ................ 260/955, 961; 514/141

[56] References Cited

U.S. PATENT DOCUMENTS

| | | | |
|---|---|---|---|
| 3,155,709 | 11/1964 | Newallis et al. | 260/961 |
| 3,209,020 | 9/1965 | Schrader | 260/961 |
| 3,354,225 | 11/1967 | Kane | 252/522 R |
| 4,190,653 | 2/1980 | Saito et al. | 260/955 |

FOREIGN PATENT DOCUMENTS 2732930 2/1978 Fed. Rep. of Germany .

*Primary Examiner*—Anton H. Sutto

*Attorney, Agent, or Firm*—Sprung Horn Kramer & Woods

[57] ABSTRACT

O-(2,2,2-trihalogenoethyl) S-alkyl (di)thiophosphonates of the formula

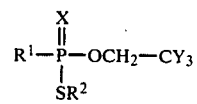

in which
X is oxygen or sulphur,
Y is halogen,
$R^1$ is alkyl or optionally substituted aryl, and
$R^2$ is alkyl.

which exhibit insecticidal, acaricidal and nematocidal activity. Intermediates therefor of the formulas

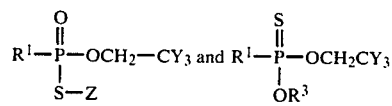

in which
Z is one equivalent of an alkali metal or ammonium ion, and
$R^3$ is $C_1$–$C_4$-alkyl, are also new.

10 Claims, No Drawings

THIOPHOSPHONIC ACID ESTER PESTICIDES

The invention relates to O-(2,2,2-trihalogenoethyl) S-(alkyl) (di)thiophosphonates, several processes for their preparation and their use as agents for combating pests, in particular as insecticides and acaricides.

It is known that certain O-(2,2,2-trihalogenoethyl) S-(alkyl) (di)thiophosphates, such as, for example, O-(ethyl) O-(2,2,2-trichloroethyl) S-(n-propyl) thiophosphate and O-(ethyl) O-(2,2,2-trifluoroethyl) S-(n-propyl) dithiophosphate, can be used for combating pests (compare DE-OS (German Published Specification) No. 2,732,930).

However, the insecticidal and acaricidal action of the known compounds is not always satisfactory, especially with low concentrations of active compound and when low amounts are applied.

New O-(2,2,2-trihalogenoethyl) S-(alkyl) (di)thiophosphonates of the formula (I)

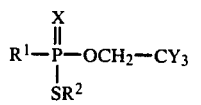
(I)

in which
X represents oxygen or sulphur,
Y represents halogen,
$R^1$ represents alkyl or optionally substituted aryl and
$R^2$ represents alkyl,
have been found.

The new compounds of the formula (I) are obtained by a process in which
(a) thiophosphonic acid derivatives of the formula (II)

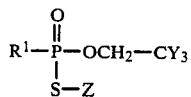
(II)

in which
$R^1$ and Y have the abovementioned meaning and
Z represents one equivalent of an alkali metal or ammonium ion,
are reacted with alkyl halides of the formula (III)

(III)

in which
$R^2$ has the abovementioned meaning and
Hal represents halogen, preferably chlorine, bromine or iodine,
if appropriate in the presence of diluents, or (b) dithiophosphonic acid ester halides of the formula (IV)

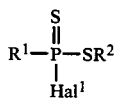
(IV)

in which
$R^1$ and $R^2$ have the abovementioned meaning and
$Hal^1$ represents halogen, preferably chlorine, bromine or iodine,
are reacted with trihalogenoethanol derivatives of the formula (V)

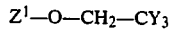
(V)

in which
Y has the abovementioned meaning and
$Z^1$ represents hydrogen or one equivalent of an alkali metal or ammonium ion,
if appropriate in the presence of acid acceptors and if appropriate in the presence of diluents.

The new O-(2,2,2-trihalogenoethyl) S-(alkyl) (di)thiophosphonates of the formula (I) are distinguished by a high activity against animal pests, in particular by a high insecticidal, acaricidal and nematicidal activity. The active compounds according to the invention can also be used for combating species of Plasmopara, such as, for example, the downy mildew of vine causative organism (Plasmopara viticola). They can also be used in synergistic mixtures with other pesticides.

Surprisingly, the compounds of the formula (1) according to the invention exhibit more advantageous insecticidal, acaricidal and nematicidal properties than corresponding known compounds.

Alkyl $R^1$ and $R^2$ represent straight-chain or branched alkyl with preferably 1 to 8, in particular 1 to 6 carbon atoms, and particularly preferably with 1 to 4 carbon atoms. Examples which may be mentioned are methyl, ethyl, n- and i-propyl and n-, i-, s- and t-butyl.

Optionally substituted aryl $R^1$ represents aryl with 6 to 10 carbon atoms, preferably optionally substituted phenyl or naphthyl, and in particular optionally substituted phenyl.

The optionally substituted aryl radical $R^1$ can carry one or more, preferably 1 to 3 and in particular 1 or 2, identical or different substituents. Examples of substituents which may be mentioned are: alkyl with preferably 1 to 4, in particular 1 or 2, carbon atoms, such as methyl, ethyl, n- and i-propyl and n-, i- and t-butyl; alkoxy with preferably 1 to 4, in particular 1 or 2, carbon atoms, such as methoxy, ethoxy, n- and i-propoxy and n-, i- and t-butoxy; alkylthio with preferably 1 to 4, in particular 1 or 2, carbon atoms, such as methylthio, ethylthio, n- and i-propylthio and n-, i- and t-butylthio; halogenoalkyl with preferably 1 to 4, in particular 1 or 2, carbon atoms and preferably 1 to 5, in particular 1 to 3, halogen atoms, the halogen atoms being identical or different and halogen atoms preferably representing fluorine, chlorine or bromine, in particular fluorine, such as trifluoromethyl; halogenoalkoxy with preferably 1 to 4, in particular 1 or 2 carbon atoms and preferably 1 to 5, in particular 1 to 3, halogen atoms, the halogen atoms being identical or different and halogen atoms preferably representing fluorine, chlorine or bromine, in particular fluorine, such as trifluoromethoxy; halogen, preferably fluorine, chlorine, bromine and iodine, in particular chlorine and bromine; cyano and nitro.

Halogen Y represents fluorine, chlorine, bromine or iodine, preferably chlorine or fluorine, Y in each case representing identical or different, preferably identical, halogen atoms.

The invention preferably relates to compounds of the formula (I) in which
X represents oxygen or sulphur,
Y represents fluorine, chlorine, bromine or iodine,
$R^1$ represents alkyl with 1 to 6 carbon atoms or an aryl radical which has 6 to 10 carbon atoms and can be substituted by one or more, preferably 1 to 3, in particular 1 or 2, identical or different substituents, preferably halogens, such as fluorine, chlorine or bromine, cyano, nitro, halogenoalkyl or halogenoalkoxy with preferably 1 to 5, in particular 1 to 3, carbon atoms and 1 to 5 identical or different halogen atoms, such as fluorine, chlorine or bromine and/or $C_1$–$C_4$-alkyl, and $R^2$ represents alkyl with 1 to 6 carbon atoms.

The invention particularly relates to compounds of the formula (I), in which

X represents oxygen or sulphur,

Y represents fluorine or chlorine, $R^1$ represents an alkyl radical with 1 to 6 carbon atoms or a phenyl radical which is optionally substituted by fluorine, chlorine, bromine, cyano, nitro, methyl, trifluoromethyl and/or trifluoromethoxy and $R^2$ represents an alkyl radical with 1 to 6 carbon atoms.

If, for example, the potassium salt of O-(2,2,2-trichloroethyl) methanethiophosphonate and ethylbromide are used as starting substances for reaction variant (a), the reaction of these compounds can be outlined by the following equation:

$$\underset{\underset{S-K}{|}}{\overset{\overset{O}{\|}}{H_3C-P-OCH_2-CCl_3}} + Br-CH_2-CH_3 \xrightarrow{-KBr}$$

$$\underset{\underset{S-CH_2-CH_3}{|}}{\overset{\overset{O}{\|}}{H_3C-P-OCH_2-CCl_3}}$$

If S-(n-propyl) methane dithiophosphonate chloride and 2,2,2-trichloroethanol are used as starting substances for reaction variant (b), the reaction of these compounds can be outlined by the following equation:

$$\underset{\underset{Cl}{|}}{\overset{\overset{S}{\|}}{H_3C-P-S-C_3H_7n}} + HO-CH_2-CCl_3 \xrightarrow{-HCl}$$

$$\underset{\underset{OCH_2CCl_3}{|}}{\overset{\overset{S}{\|}}{H_3C-P-S-C_3H_7n}}$$

The formula (II) provides a definition of the new thiophosphonic acid derivatives to be used as the starting substances in process variant (a) according to the invention. In this formula, R' and Y have the meaning given above in the case of formula (I). Z represents one equivalent of an alkali metal (preferably sodium, potassium or lithium) or ammonium ion.

Examples which may be mentioned of compounds of the formula (II) are: the sodium, potassium, lithium and ammonium salts of: O-2,2,2-trichloroethyl, -trifluoroethyl or -tribromoethyl methane-, ethane-, n-propane-, i-propane-, n-butane-, i-butane-, sec.-butane- and tert.-butane-thiophosphonate; and O-2,2,2-trifluoroethyl or -trichloroethyl or -tribromoethyl phenyl-, 2-chloro-, 2-bromo-, 4-fluoro-, 4-chloro-, 4-bromo-, 4-methyl-, 4-trifluoromethyl, 4-trifluoromethoxy-, 4-nitro-, 4-cyano-, 2,4-difluoro-, 2,4-dichloro-, 2,4-dibromo-, 3,4-dichloro-, 2,6-dimethyl-, 2,6-dichloro- and 2,6-dibromophenyl-thiophosphonate.

The compounds of the formula (II) are new and are part of the present invention. The preferred substituents mentioned for the compounds of the formula (I) also apply to the compounds of the formula (II). The thiophosphonic acid derivatives of the general formula (II) are obtained by a process in which, for example, thiophosphonic acid esters of the formula (VI)

$$\underset{\underset{OR^3}{|}}{\overset{\overset{S}{\|}}{R^1-P-OCH_2CY_3}} \quad (VI)$$

in which $R^1$ and Y have the abovementioned meaning and $R^3$ represents $C_1$–$C_4$-alkyl, are heated with xanthates of the formula (VII)

$$\overset{\overset{S}{\|}}{Z-S-C-OR^4} \quad (VII)$$

in which

Z has the abovementioned meaning and $R^4$ represents $C_1$–$C_4$-alkyl, if appropriate in the presence of diluents, such as, for example, acetonitrile, at the boiling point of the diluent (compare the preparation examples).

The formula (VI) provides a definition of the thiophosphonic acid esters required as starting substances. In this formula, $R^1$ and Y have the meaning given in the case of formula (I). $R^3$ preferably represents methyl, ethyl, n-propyl, i-propyl, n-butyl or i-butyl.

Examples which may be mentioned of the compounds of the formula (VI) are: O-methyl, O-ethyl, O-n-propyl, O-i-propyl and O-n-butyl (2,2,2-trichloroethyl) methanethionophosphonate; O-methyl, O-ethyl, O-n-propyl, O-i-propyl and O-n-butyl (2,2,2-trifluoroethyl) methanethionophosphonate; O-methyl, O-ethyl, O-n-propyl, O-i-propyl and O-n-butyl (2,2,2-tribromoethyl) methanethionophosphonate; O-methyl, O-ethyl, O-n-propyl, O-i-propyl and O-n-butyl (2,2,2-trifluoroethyl) ethanethionophosphonate; O-methyl, O-ethyl, O-n-propyl, O-i-propyl and O-n-butyl (2,2,2-trichloroethyl) ethanethionophosphonate; O-methyl, O-ethyl, O-n-propyl, O-i-propyl and O-n-butyl (2,2,2-tribromoethyl) ethanethionophosphonate; O-methyl, O-ethyl, O-n-propyl, O-i-propyl and O-n-butyl (2,2,2-trifluoroethyl) n-propanethionophosphonate; O-methyl, O-ethyl, O-n-propyl, O-i-propyl and O-n-butyl (2,2,2-trichloroethyl) n-propanethionophosphonate; O-methyl, O-ethyl, O-n-propyl, O-i-propyl and O-n-butyl (2,2,2-tribromoethyl) n-propanethionophosphonate; O-methyl, O-ethyl, O-n-propyl, O-i-propyl and O-n-butyl (2,2,2-trifluoroethyl) i-propanethionophosphonate; O-methyl, O-ethyl, O-n-propyl, O-i-propyl and O-n-butyl (2,2,2-trichloroethyl) i-propanethionophosphonate; O-methyl, O-ethyl, O-n-propyl, O-i-propyl and O-n-butyl (2,2,2-tribromoethyl) i-propanethionophosphonate; O-methyl, O-ethyl, O-n-propyl, O-i-propyl and O-n-butyl (2,2,2-trifluoroethyl) n-butanethionophosphonate; O-methyl, O-ethyl, O-n-propyl, O-i-propyl and O-n-butyl (2,2,2-trichloroethyl) n-butanethionophosphonate; O-methyl, O-ethyl, O-n-propyl, O-i-propyl and O-n-butyl (2,2,2-tribromoethyl) n-butanethionophosphonate; O-methyl, O-ethyl, O-n-propyl, O-i-propyl and O-n-butyl (2,2,2-trifluoroethyl) i-butanethionophosphonate; O-methyl, O-ethyl, O-n-propyl, O-i-propyl and O-n-butyl (2,2,2-trichloroethyl) i-butanethionophosphonate; O-methyl, O-ethyl, O-n-propyl, O-i-propyl and O-n-butyl (2,2,2-tribromoethyl) i-butanethionophosphonate; O-methyl, O-ethyl, O-n-propyl, O-i-propyl and O-n-butyl (2,2,2-trifluoroethyl) sec.-butanethionophosphonate; O-methyl, O-ethyl, O-n-propyl, O-i-propyl and O-n-butyl (2,2,2-trichloroethyl) sec.-butanethionophosphonate; O-methyl, O-ethyl, O-n-propyl, O-i-propyl and O-n-butyl (2,2,2-tribromoethyl) sec. butanethionophosphonate; O-methyl, O-ethyl, O-n-propyl, O-i-propyl and O-n-butyl (2,2,2-trifluoroethyl) tert.-butanethionophosphonate; O-methyl, O-ethyl, O-n-propyl, O-i-propyl and O-n-butyl (2,2,2-trichloroethyl) tert.-butanethionophosphonate; O-methyl, O-ethyl, O-n-propyl, O-i-propyl and O-n-butyl (2,2,2-tribromoethyl) tert.-butanethionophosphonate; O-methyl, O-ethyl, O-n-propyl, O-i-propyl and O-n-butyl (2,2,2-trifluoroethyl) n-pentanethionophosphonate; O-methyl, O-ethyl, O-n-propyl, O-i-propyl and O-n-butyl (2,2,2-trichloroethyl) n-pentanethionophosphonate; O-methyl, O-ethyl, O-n-propyl, O-i-propyl and O-n-butyl (2,2,2-tribromoethyl) n-pentanethionophosphonate; O-methyl, O-ethyl, O-n-propyl, O-i-propyl and O-n-butyl (2,2,2-trifluoroethyl) i-pentanethionophosphonate; O-methyl, O-ethyl, O-n-propyl, O-i-propyl and O-n-butyl (2,2,2-trichloroethyl) i-pentanethionophosphonate; O-methyl, O-ethyl, O-n-propyl, O-i-propyl and O-n-butyl (2,2,2-tribromoethyl) i-pentanethionophosphonate; O-methyl, O-ethyl, O-n-propyl, O-i-propyl and O-n-butyl (2,2,2-trifluoroethyl) 2,2-dimethyl-propanethionophosphonate; O-methyl, O-ethyl, O-n-propyl, O-i-propyl and O-n-butyl (2,2,2-trichloroethyl) 2,2-dimethyl-propanethionophosphonate; O-methyl, O-ethyl, O-n-propyl, O-i-propyl and O-n-butyl (2,2,2-tribromoethyl) 2,2-dimethyl-propanethionophosphonate; O-methyl, O-ethyl, O-n-propyl, O-i-propyl and O-n-butyl (2,2,2-trifluoroethyl) n-hexanethionophosphonate; O-methyl, O-ethyl, O-n-propyl, O-i-propyl and O-n-butyl (2,2,2-trichloroethyl) n-hexanethionophosphonate; O-methyl, O-ethyl, O-n-propyl, O-i-propyl and O-n-butyl (2,2,2-tribromoethyl) n-hexanethionophosphonate; O-methyl, O-ethyl, O-n-propyl, O-i-propyl and O-n-butyl (2,2,2-trifluoroethyl) 2,3-dimethylbutanethionophosphonate; O-methyl, O-ethyl, O-n-propyl, O-i-propyl and O-n-butyl (2,2,2-trichloroethyl) 2,3-dimethylbutanethionophosphonate; O-methyl, O-ethyl, O-n-propyl, O-i-propyl and O-n-butyl (2,2,2-tribromoethyl) 2,3-dimethylbutanethionophosphonate; O-methyl, O-ethyl, O-n-propyl, O-i-propyl and O-n-butyl (2,2,2-trifluoroethyl) 2,2-dimethyl-butanethionophosphonate; O-methyl, O-ethyl, O-n-propyl, O-i-propyl and O-n-butyl (2,2,2-trichloroethyl) 2,2-dimethylbutanethionophosphonate; O-methyl, O-ethyl, O-n-propyl, O-i-propyl and O-n-butyl (2,2,2-tribromoethyl) 2,2-dimethylbutanethionophosphonate; O-methyl, O-ethyl, O-n-propyl, O-i-propyl and O-n-butyl (2,2,2-trifluoroethyl) 2-methyl-pentanethionophosphonate; O-methyl, O-ethyl, O-n-propyl, O-i-propyl and O-n-butyl (2,2,2-trichloroethyl) 2-methyl-pentanethionophosphonate; O-methyl, O-ethyl, O-n-propyl, O-i-propyl and O-n-butyl (2,2,2-tribromoethyl) 2-methyl-pentanethionophosphonate; O-methyl, O-ethyl, O-n-propyl, O-i-propyl and O-n-butyl (2,2,2-trifluoroethyl) phenyl-thionophosphonate; O-methyl, O-ethyl, O-n-propyl, O-i-propyl and O-n-butyl (2,2,2-trichloroethyl) phenyl-thionophosphonate; O-methyl, O-ethyl, O-n-propyl, O-i-propyl and O-n-butyl (2,2,2-tribromoethyl) phenyl-thionophosphonate; O-methyl, O-ethyl, O-n-propyl, O-i-propyl and O-n-butyl (2,2,2-trifluoroethyl) (2-chlorophenyl)-thionophosphonate; O-methyl, O-ethyl, O-n-propyl, O-i-propyl and O-n-butyl, (2,2,2-trichloroethyl) (2-chlorophenyl)-thionophosphonate; O-methyl, O-ethyl, O-n-propyl, O-i-propyl and O-n-butyl (2,2,2-tribromoethyl) (2-chlorophenyl)-thionophosphonate; O-methyl, O-ethyl, O-n-propyl, O-i-propyl and O-n-butyl (2,2,2-trifluoroethyl) (2-bromophenyl)-thionophosphonate; O-methyl, O-ethyl, O-n-propyl, O-i-propyl and O-n-butyl (2,2,2-trichloroethyl) (2-bromophenyl)-thionophosphonate; O-methyl, O-ethyl, O-n-propyl, O-i-propyl and O-n-butyl (2,2,2-tribromoethyl) (2-bromophenyl)-thionophosphonate; O-methyl, O-ethyl, O-n-propyl, O-i-propyl and O-n-butyl (2,2,2-trifluoroethyl) (4-fluorophenyl)-thionophosphonate; O-methyl, O-ethyl, O-n-propyl, O-i-propyl and O-n-butyl (2,2,2-trichloroethyl) (4-fluorophenyl)-thionophosphonate; O-methyl, O-ethyl, O-N-propyl, O-i-propyl and O-n-butyl (2,2,2-tribromoethyl) (4-fluorophenyl)-thionophosphonate; O-methyl, O-ethyl, O-n-propyl, O-i-propyl and O-n-butyl (2,2,2-trifluoroethyl) (4-chlorophenyl)-thionophosphonate; O-methyl, O-ethyl, O-n-propyl, O-i-propyl and O-n-butyl (2,2,2-trichloroethyl) (4-chlorophenyl)-thionophosphonate; O-methyl, O-ethyl, O-n-propyl, O-i-propyl and O-n-butyl (2,2,2-tribromoethyl) (4-chlorophenyl)-thionophosphonate; O-methyl, O-ethyl, O-n-propyl, O-i-propyl and O-n-butyl (2,2,2-trifluoroethyl) (4-bromophenyl)-thionophosphonate; O-methyl, O-ethyl, O-n-propyl, O-i-propyl and O-n-butyl (2,2,2-trichloroethyl) (4-bromophenyl)-thionophosphonate; O-methyl, O-ethyl, O-n-propyl, O-i-propyl and O-n-butyl (2,2,2-tribromoethyl) (4-bromophenyl)-thionophosphonate; O-methyl, O-ethyl, O-n-propyl, O-i-propyl and O-n-butyl (2,2,2-trifluoroethyl) (4-methylphenyl)-thionophosphonate; O-methyl, O-ethyl, O-n-propyl, O-i-propyl and O-n-butyl (2,2,2-trichloroethyl) (4-methylphenyl)-thionophosphonate; O-methyl, O-ethyl, O-n-propyl, O-i-propyl and O-n-butyl (2,2,2-tribromoethyl) (4-methylphenyl)-thionophosphonate; O-methyl, O-ethyl, O-n-propyl, O-i-propyl and O-n-butyl (2,2,2-trifluoroethyl) (4-trifluoromethylphenyl)-thionophosphonate; O-methyl, O-ethyl, O-n-propyl, O-i-propyl and O-n-butyl (2,2,2-trichloroethyl) (4-trifluoromethylphenyl)-thionophosphonate; O-methyl, O-ethyl, O-n-propyl, O-i-propyl and O-n-butyl (2,2,2-tribromoethyl) (4-trifluoromethylphenyl)-thionophosphonate; O-methyl, O-ethyl, O-n-propyl, O-i-propyl and O-n-butyl (2,2,2-trifluoroethyl) (4-trifluoromethoxyphenyl)-thionophosphonate; O-methyl, O-ethyl, O-n-propyl, O-i-propyl and O-n-butyl (2,2,2-trichloroethyl) (4-trifluoromethoxyphenyl)-thionophosphonate; O-methyl, O-ethyl, O-n-propyl, O-i-propyl and O-n-butyl (2,2,2-tribromoethyl) (4-trifluoromethoxyphenyl)-thionophosphonate; O-methyl, O-ethyl, O-n-propyl, O-i-propyl and O-n-butyl (2,2,2-trifluoroethyl) (4-nitrophenyl)-thionophosphonate; O-methyl, O-ethyl, O-n-propyl, O-i-propyl and O-n-butyl (2,2,2-trichloroethyl) (4-nitrophenyl)-thionophosphonate; O-methyl, O-ethyl, O-n-propyl, O-i-propyl and O-n-butyl (2,2,2-tribromoethyl) (4-nitrophenyl)-thionophosphonate; O-methyl, O-ethyl, O-n-propyl, O-i-propyl and O-n-butyl (2,2,2-trifluoroethyl) (4-cyanophenyl)-thionophosphonate; O-methyl, O-ethyl, O-n-propyl, O-i-propyl and O-n-butyl (2,2,2-trichloroethyl) (4-cyanophenyl)-thionophosphonate; O-methyl, O-ethyl, O-n-propyl, O-i-propyl and O-n-butyl (2,2,2-tribromoethyl) (4-cyanophenyl)-thionophosphonate; O-methyl, O-ethyl, O-n-propyl, O-i-propyl and O-n-butyl (2,2,2-trifluoroethyl) (2,4-difluorophenyl)-thionophosphonate; O-methyl, O-ethyl, O-n-propyl, O-i-propyl and O-n-butyl (2,2,2-trichloroethyl) (2,4-difluorophenyl)-thionophosphonate; O-methyl, O-ethyl, O-n-propyl, O-i-propyl and O-n-butyl (2,2,2-tribromoethyl) (2,4-difluorophenyl)-thionophosphonate; O-methyl, O-ethyl, O-n-propyl, O-i-propyl and O-n-butyl (2,2,2-trifluoroethyl) (2,4-dichlorophenyl)-thionophosphonate; O-methyl, O-ethyl, O-n-propyl, O-i-propyl and O-n-butyl (2,2,2-trichloroethyl) (2,4-dichlorophenyl)-thionophosphonate; O-methyl, O-ethyl, O-n-propyl, O-i-propyl and O-n-butyl (2,2,2-tribromoethyl) (2,4-dichlorophenyl)-thionophosphonate; O-methyl, O-ethyl, O-n-propyl, O-i-propyl and O-n-butyl (2,2,2-trifluoroethyl) (2,4-dibromophenyl)-thionophosphonate; O-methyl, O-ethyl, O-n-propyl, O-i-propyl and O-n-butyl (2,2,2-trichloroethyl) (2,4-dibromophenyl)-thionophosphonate; O-methyl, O-ethyl, O-n-propyl, O-i-propyl and O-n-butyl (2,2,2-tribromoethyl) (2,4-dibromophenyl)-thionophosphonate; O-methyl, O-ethyl, O-n-propyl, O-i-propyl and O-n-butyl (2,2,2-trifluoroethyl) (3,4-dichlorophenyl)-thionophosphonate; O-methyl, O-ethyl, O-n-propyl, O-i-propyl and O-n-butyl (2,2,2-trichloroethyl) (3,4-dichlorophenyl)-thionophosphonate; O-methyl, O-ethyl, O-n-propyl, O-i-propyl and O-n-butyl (2,2,2-tribromoethyl) (3,4-dichlorophenyl)-thionophosphonate; O-methyl, O-ethyl, O-n-propyl, O-i-propyl and O-n-butyl (2,2,2-trifluoroethyl) (2,6-dimethylphenyl)-thionophosphonate; O-methyl, O-ethyl, O-n-propyl, O-i-propyl and O-n-butyl (2,2,2-trichloroethyl) (2,6-dimethylphenyl)-thionophosphonate; O-methyl, O-ethyl, O-n-propyl, O-i-propyl and O-n-butyl (2,2,2-tribromoethyl) (2,6-dimethylphenyl)-thionophosphonate; O-methyl, O-ethyl, O-n-propyl, O-i-propyl and O-n-butyl, (2,2,2-trifluoroethyl) (2,6-dichlorophenyl)-thionophosphonate; O-methyl, O-ethyl, O-n-propyl, O-i-propyl and O-n-butyl (2,2,2-trichloroethyl) (2,6-dichlorophenyl)-thionophosphonate; O-methyl, O-ethyl, O-n-propyl, O-i-propyl and O-n-butyl (2,2,2-tribromoethyl) (2,6-dichlorophenyl)-thionophosphonate; O-methyl, O-ethyl, O-n-propyl, O-i-propyl and O-n-butyl (2,2,2-trifluoroethyl) (2,6-dibromophenyl)-thionophosphonate; O-methyl, O-ethyl, O-n-propyl, O-i-propyl and O-n-butyl (2,2,2-trichloroethyl) (2,6-dibromophenyl)-thionophosphonate and O-methyl, O-ethyl, O-n-propyl, O-i-propyl and O-n-butyl, (2,2,2-tribromoethyl) (2,6-dibromophenyl)-thionophosphonate, the 2,2,2-trihaloalkyl groups being bonded to the P-atom via an oxygen atom.

The compounds of the formula VI required as starting substances are new. They are prepared in a known manner by generally customary methods, for example by adding thionophosphonic acid halides to trihalogeno alcohols in the presence of strong bases or organometallic compounds, such as, for example, butyl-lithium, at temperatures between 20° C. and 60° C. (compare the preparation examples).

The formula (VII) provides a definition of the xanthates also required as starting substances. In the formula, $R^4$ represents $C_1-C_4$-alkyl and Z preferably represents a sodium, potassium, lithium or ammonium ion.

Examples which may be mentioned of compounds of the formula (VII) are: theسodium, potassium, lithium and ammonium salts of methyl, ethyl, n-propyl, i-propyl, n-butyl and i-butyl xanthate.

The xanthates of the formula (VII) are generally known compounds of organic chemistry.

The formula (III) provides a definition of the alkyl halides also to be used as starting substances for process variant (a) according to the invention. In this formula, $R^2$ has the meaning given in the case of the formula (I).

Hal represents halogen, preferably chlorine, bromine or iodine.

Examples which may be mentioned of compounds of the formula (III) are: methyl, ethyl, n-propyl, i-propyl, n-butyl, i-butyl, sec.-butyl and tert.-butyl chloride, bromide and iodide.

The compounds of the formula (III) are generally known compounds of organic chemistry.

The formula (IV) provides a definition of the dithiophosphonic acid ester halides to be used as starting substances in process variant (b) according to the invention. In this formula, $R^1$ and $R^2$ have the meaning given above in the case of formula (I). $Hal^1$ represents halogen, preferably chlorine or bromine.

Examples which may be mentioned of compounds of the formula (IV) are: S-methyl, S-ethyl, S-n-propyl, S-i-propyl, S-n-butyl, S-i-butyl, S-sec.-butyl, S-tert.-butyl, S-n-pentyl, S-i-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)methanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)ethanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)n-propanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)i-propanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)n-butanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)i-butanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)sec.-butanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)tert.-butanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)n-pentanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-2,3-dimethyl-butyl), S-(2,2-dimethyl-butyl) and S-(2-methyl-pentyl)i-pentanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)2,2-dimethyl-propanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)n-hexanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)2,3-dimethyl-butanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)2,2-dimethyl-butanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)2-methyl-pentanedithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)phenyldithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(2-chlorophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(2-bromophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(4-fluorophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-phenyl)(4-chlorophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl, S-(2,2-dimethyl-butyl) and S-(2-methyl-pentyl)(4-bromophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl and S-(2-methyl-pentyl)(4-methylphenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(4-trifluoromethyl-phenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(4-trifluoromethoxyphenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(4-nitrophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(4-cyanophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-2-methyl-pentyl)(2,4-difluorophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(2,4-dichlorophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(2,4-dibromophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(3,4-dichlorophenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(2,6-dimethylphenyl)-dithiophosphonate chloride and bromide; S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(2,6-dichlorophenyl)-dithiophosphonate chloride and bromide and S-methyl, S-ethyl, S-n-propyl, S-i-propyl, S-n-butyl, S-i-butyl, S-sec.-butyl, S-tert.-butyl, S-n-pentyl, S-i-pentyl, S-(2,2-dimethyl-propyl), S-n-hexyl, S-(2,3-dimethyl-butyl), S-(2,2-dimethyl-butyl) and S-(2-methyl-pentyl)(2,6-dibromophenyl)-dithiophosphonate chloride and bromide.

The compounds of the formula (IV) are known (compare European Pat. No. 25,270 and U.S. Ser. No. 867,261, filed Jan. 5, 1978, now pending.

The formula (V) provides a definition of the trihalogenoethanol derivatives also required in process variant (b). In this formula, Y preferably represents fluorine, chlorine or bromine and Z preferably represents a sodium, potassium, lithium or ammonium ion.

Examples which may be mentioned of compounds of the formula (V) are: sodium, potassium, lithium or ammonium trifluoro-, trichloro- and tribromo-ethanolate.

The compounds of the formula (V) are generally known compounds of organic chemistry.

Possible diluents for process variant (a) according to the invention are virtually all the inert organic diluents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbontetrachloride, chlorobenzene and o-dichlorobenzene, ethers, such as diethyl ether and dibutyl ether, glycoldimethyl ether and diglycoldimethyl ether, tetrahydrofuran and dioxane, ketones, such as acetone, methylethyl ketone, methylisopropyl ketone and methylisobutyl ketone, esters, such as methyl and ethyl acetate, nitriles, such as, for example, acetonitrile and propionitrile, amides, such as, for example, dimethylformamide, dimethylacetamide and N-methylpyrrolidone, and dimethylsulphoxide, tetramethylenesulphone and hexamethylphosphoric acid triamide.

Process (a) according to the invention is in general carried out at temperatures between 0° C. and 120° C. The range between 20° C. and 100° C. is preferred. The reactions are in general carried out under normal pressure.

For carrying out process (a) according to the invention, 1.2 to 2 mols, preferably 1.4 to 1.8 mols, of alkyl halide of the formula (III) are employed per mol of thiophosphonic acid derivative of the formula (II).

The reaction is in general carried out in a suitable diluent. Working up is effected by customary methods. The new compounds are in some cases obtained in the form of oils, some of which cannot be distilled without decomposition, but are freed from the last volatile constituents by so-called "incipient distillation", that is to say by prolonged heating to moderately elevated temperatures under reduced pressure, and are purified in this manner. They are characterized by their refractive index.

Virtually all the inert organic diluents can be used as diluents for process variant (b) according to the invention. The diluents which have been mentioned in connection with the description of process (a) according to the invention are preferably used.

If appropriate, process (b) can be carried out in the presence of acid acceptors. All the customary acid-binding agents can be used as acid acceptors. Alkali metal carbonates and alcoholates, such as sodium and potassium carbonate and sodium or potassium methylate or ethylate, and furthermore aliphatic, aromatic or heterocyclic amines, for example triethylamine, trimethylamine, dimethylaniline, dimethylbenzylamine and pyridine, have proved particularly suitable.

Process (b) according to the invention is in general carried out at temperatures between −20° C. and +110° C. The range between 20° C. and 80° C. is preferred.

The reactions are in general carried out under normal pressure.

For carrying out process (b) according to the invention, 1 to 1.6 mols, preferably 1.1 to 1.4 mols, of trihalogenoethanol derivative of the formula (V) are employed per mol of the compound of the formula (IV).

The reaction is in general carried out in a suitable diluent and if appropriate in the presence of an acid acceptor. Working up is effected by customary methods.

The new compounds are in some cases obtained in the form of oils, some of which cannot be distilled without decomposition, but are freed from the last volatile constituents by so-called "incipient distillation", that is to say by prolonged heating to moderately elevated temperatures under reduced pressure, and are purified in this manner. They are characterized by their refractive index.

The active compounds are well tolerated by plants and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euselis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carposcapsa pomonella,* Pieris spp., Chilo spp., *Pyrausta nubilalis, Ephestria kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceu-* thorrhynchus assimilis, *Hypera postica*, Dermestes spp., Trogoderma spp., Anthrenus spp., Attagenus spp., Lyctus spp., *Meligethes aeneus*, Ptinus spp., *Niptus hololecucus, Gibbium psylloides*, Tribolium spp., *Tenebrio molitor*, Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., and Tetranychus spp.

The plant-parasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp., and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are prepared in a known manner, for example by mixing the active compounds with extenders, that is, liquid solvents, liquified gases under pressure, and/or solid carriers, optionally with the use of surface-active agents, that is, emulsifying agents and/or dispersing agents, and/or foam forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquified gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of livestock husbandry and animal breeding, where better results, for example higher milk yields, higher weight, longer life and the like, can be achieved by combating the pests.

In these fields, the active compounds according to the invention are used in a known manner, preferably by dermal application in the form of dipping (dips), spraying (sprays), pouring (pour-on and spot-on) and dusting.

The preparation of the compounds according to the invention may be illustrated with the aid of the following examples:

EXAMPLE 1

(Process Variant (a))

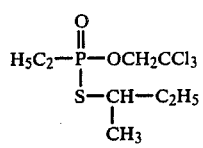

20 g (0.068 mol) of the potassium salt of O-2,2,2-trichloroethyl ethanethiophosphonate are heated to 80° C. in 150 ml of acetonitrile with 13.7 g (0.1 mol) of 2-bromobutane for 18 hours. The solvent is then removed in vacuo. The residue is taken up in 300 ml of methylene chloride and the mixture is washed with dilute sodium hydroxide solution and then with water. The organic phase is dried over magnesium sulphate and the solvent is removed by vacuum distillation.

8.6 g (40% of theory) of S-1-methyl-propyl O-2,2,2-trichloroethyl ethanethiophosphonate of refractive index $n_D^{20}$: 1.5325 are obtained. Precursors (Compounds of the formula II):

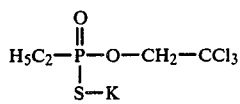

75 g (0.263 mol) of O-ethyl-O-2,2,2-trichloroethyl ethanethiophosphonate and 42.1 g (0.263 mol) of potassium xanthogenate are heated under reflux in 300 ml of acetonitrile until the starting substance has reacted completely (about 48 hours). After the mixture has been cooled and the solvent has been removed in vacuo, the residue is washed several times with an ether/hexane mixture and is then projected to incipient distillation.

40 g (52% of theory) of the potassium salt of O-2,2,2-trichloroethyl ethanethiophosphonate are obtained.

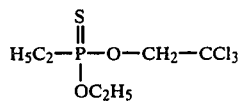

A 20% strength solution of 33.9 g (0.53 mol) of butyl-lithium in n-hexane is added to dropwise to a mixture of 74.7 g (0.5 mol) of 2,2,2-trichloroethanol and 500 ml of tetrahydrofuran at −60° C. The mixture is warmed slowly to 20° C. and 86 g (0.5 mol) of O-ethyl ethanethiophosphonic acid ester chloride are added dropwise. After the mixture has been stirred at 20° C. for 18 hours, it is warmed to 60° C. for 1 hour and cooled and the solvent is removed in vacuo. After the residue has been taken up in 300 ml of methylene chloride, the mixture is washed with dilute sodium hydroxide solution and then with water. The organic phase is separated off and dried over magnesium sulphate. The solvent is removed in vacuo.

77.5 g (54% of theory) of O-ethyl O-2,2,2-trichloroethyl ethanethiophosphonate of refractive index $n_D^{20}$: 1.5128 are obtained.

The remaining compounds of the formula II are obtained in a corresponding manner.

EXAMPLE 2

(Process Variant (b))

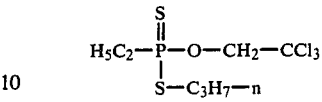

33 g of a 15% strength butyl-lithium solution are added dropwise to a mixture of 16.4 g (0.11 mol) of 2,2,2-trichlorethanol and 150 ml of tetrahydrofuran at −55° C. and the mixture is subsequently stirred at −55° C. for 30 minutes. After the mixture has been warmed to +20° C., 22 g (0.1 mol) of S-n-propyl ethanedithiophosphonate chloride are added dropwise and the mixture is stirred at +20° C. for 18 hours. The solvent is then removed under a water-pump vacuum. The residue is taken up in methylene chloride and the solution is washed alkaline and then neutral. The organic phase is dried over magnesium sulphate and the solvent is removed under a water-pump vacuum.

27.2 g (86% of theory) of S-n-propyl O-2,2,2-trichloroethyl ethanedithiophosphonate of refractive index $n_D^{20}$: 1.5400 are obtained.

The following compounds of the formula (I) are obtained analogously to Example 1 and 2 or process variant (a) and (b):

TABLE A $$R^1-\underset{\underset{SR^2}{|}}{\overset{\overset{X}{\|}}{P}}-OCH_2-CY_3 \quad (I)$$

| Example No. | $R^1$ | $R^2$ | X | Y | Refractive index: $n_D^{20}$ |
|---|---|---|---|---|---|
| 3 | CH₃ | n-C₃H₇ | S | F | 1,4780 |
| 4 | C₂H₅ | sec.C₄H₉ | S | F | 1,4552 |
| 5 | C₂H₅ | n-C₃H₇ | S | F | 1,4711 |
| 6 | –C₆H₅ | sec.C₄H₉ | S | F | 1,5308 |
| 7 | CH₃ | sec.C₄H₉ | S | F | 1,4750 |
| 8 | CH₃ | n-C₃H₇ | S | Cl | 1,5465 |
| 9 | C₂H₅ | sec.C₄H₉ | S | Cl | 1,5388 |
| 10 | CH₃ | n-C₃H₇ | O | F | 1,4425 |
| 11 | C₂H₅ | n-C₃H₇ | O | F | 1,5093 |
| 12 | C₂H₅ | –CH(C₂H₅)(CH₃) | O | F | 1,4356 |
| 13 | C₂H₅ | n-C₃H₇ | O | Cl | 1,5380 |
| 14 | CH₃ | –CH(C₂H₅)(CH₃) | O | F | 1,4672 |

The biological activity of the new active compounds of the formula I may be illustrated with the aid of the following biological examples.

The compounds of the following formulae wre used as comparison compounds:

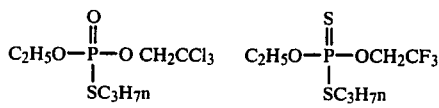

(known from DE-OS (German Published Specification No. 2,732,930)

Example A

Critical concentration test/soil insects
Test insect: *Phorbia antiqua* maggots (in the soil)
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practially no importance, only the amount by weight of active compound per unit volume of soil, which is given in ppm (=mg/lit), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of Preparation Examples (1), (2), (3), (4), (5), (7), (9), (12) and (13), showed a destruction of 100%, whereas the comparison compound A resulted in no destruction (0%), at an active compound concentration of 5 ppm.

Example B

Plutella test
Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified period of time, the destruction in % is determined. 100% means that all the caterpillars have been killed; 0% means that none of the caterpillars have been killed.

In this test, for example, the compounds of Preparation Examples (1), (2), (8), (9), (10), (12), (13) and (14) showed a destruction of 100% after 3 days at an active compound concentration of 0.01%, whereas the comparison compound (B) resulted in no destruction (0%).

Example C

Tetranychus test (resistant)
Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified period of time, the destruction in % is determined. 100% means that all the spider mites have been killed; 0% means that none of the spider mites have been killed.

In this test, for example, the compounds of Preparation Examples (1), (2), (8) and (13) showed a destruction of 95 to 100% after 2 days at an active compound concentration of 0.1%, whereas the comparison compound (B) resulted in no destruction (0%).

Example D

Test with parasite fly larvai (*Lucilia cuprina*)
Solvent: 35 parts by weight of ethylene glycol monomethyl ether
Emulsifier: 35 parts by weight of nonylphenol polyglycol ether To produce a suitable preparation of active compound, 30 parts by weight of the particular active substance are mixed with the stated amount of solvent which contains the abovementioned amount of emulsifier, and the concentrate thus obtained is diluted with water to the desired concentration.

About 20 fly larvae (*Lucilia cuprina*) are introduced into a test tube which contains about 2 cm3 of horse muscle. 0.5 ml of the preparation of active compound are introduced onto this horse muscle. After 24 hours, the degree of destruction in % is determined. 100% means that all the larvae have been killed, and 0% (control) means that none of the larvae have been killed.

In a test, for example with an active compound concentration of 100 ppm, the compounds of Preparation Examples (5) and (7), for example, showed a destruction of 100%.

Example E

Critical concentration test/nematodes
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

in this test, for example, the compounds from the Preparation Examples 1 to 4, 12 and 13 show a 100% activity with an active compound concentration of 10 ppm.

It will be understood that the specification and examples are illustrative but not limitative of the present invention and that other embodiments within the spirit and scope of the invention will suggest themselves to those skilled in the art.

What is claimed is:

1. An O-(2,2,2-trihlogenoethyl) S-alkyl (di)thiophosphonate of the formula

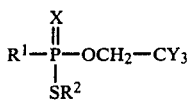

in which
X is oxygen or sulphur,
Y is halogen,
R$^1$ is methyl, ethyl or phenyl, and
R$^2$ is n-propyl or sec-butyl.

2. A compound according to claim 1, in which
Y is fluorine or chlorine, and
R$^1$ is methyl or ethyl.

3. A compound according to claim 1, wherein such compound is S-1-methyl-propyl O-2,2,2-trichloroethyl ethanethiophosphonate of the formula

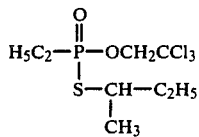

4. A compound according to claim 1, wherein such compound is S-n-propyl O-2,2,2-trichloroethyl ethanedithiophosphonate of the formula

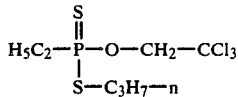

5. A compound according to claim 1, wherein such compound is S-sec.-butyl O-2,2,2-trichloroethyl ethanedithiophosphonate of the formula

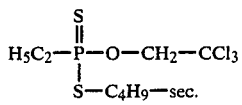

6. A compound according to claim 1, wherein such compound is S-sec.-butyl O-2,2,2-trifluoroethyl ethanethiophosphonate of the formula

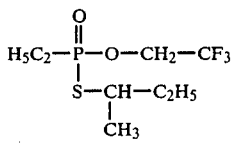

7. A compound according to claim 1, wherein such compound is S-n-propyl O-2,2,2-trichloroethyl ethanethiophosphonate of the formula

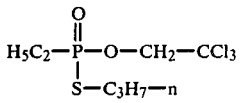

8. An insectididal, acaricidal and nematocidal composition comprising an insecticidally, acaricidally or nematocidally effective amount of a compound according to claim 1 in admixture with a diluent.

9. A method of combating insects, acarids and nematodes which comprises administering to such insects, acarids or nematodes or to a habitat thereof an insecticidally, acaricidally or nematocidally effective amount of a compound according to claim 1.

10. The method according to claim 11, wherein such compound is
S-1-methyl-propyl O-2,2,2-trichloroethyl ethanethiophosphonate,
S-n-propyl O-2,2,2-trichloroethyl ethanedithiophosphonate,
S-sec.-butyl O-2,2,2-trichloroethyl ethanedithiophosphonate,
S-sec.butyl O-2,2,2-trifluoroethyl ethanethiophosphonate, or
S-n-propyl O-2,2,2-trichloroethyl ethanethiophosphonate.

* * * * *

UNITED STATES PATENT AND TRADEMARK OFFICE
CERTIFICATE OF CORRECTION

PATENT NO. : 4,548,931

DATED : October 22, 1985

INVENTOR(S) : Bernd-Wieland Krüger, et al.

It is certified that error appears in the above-identified patent and that said Letters Patent is hereby corrected as shown below:

| | |
|---|---|
| Col. 6, line 13 | End of line delete "N" and substitute --n-- |
| Col. 12, line 57 | Delete "Ephestria" and substitute --Ephestia-- |
| Col. 13, lines 3,4 | Delete "hololecucus" and substitute --hololeucus-- |
| Col. 16, line 67 | Correct spelling of "were" |
| Col. 17, line 1 | Under structure on left insert --"Comparison compound A" and under structure on right insert --"Comparison Compound B"-- |
| Col. 18, line 24 | Correct spelling of "larvae" |

Signed and Sealed this

Fourth Day of March 1986

[SEAL]

Attest:

DONALD J. QUIGG

Attesting Officer

Commissioner of Patents and Trademarks